United States Patent [19]

Fjare

[11] Patent Number: 4,740,614

[45] Date of Patent: Apr. 26, 1988

[54] PROCESS FOR PREPARATION OF P-HYDROXYBENZOIC ACID FROM P-METHOXYTOLUENE

[75] Inventor: Kristi A. Fjare, Naperville, Ill.

[73] Assignee: Amoco Corporation, Chicago, Ill.

[21] Appl. No.: 16,745

[22] Filed: Feb. 19, 1987

[51] Int. Cl.$^4$ .......................................... C07C 51/255
[52] U.S. Cl. ..................................... 562/416; 562/475
[58] Field of Search ................................ 562/416, 475

[56] References Cited

FOREIGN PATENT DOCUMENTS 842998 8/1960 United Kingdom .

Primary Examiner—Paul J. Killos
Attorney, Agent, or Firm—Gunar J. Blumberg; William H. Magidson; Ralph C. Medhurst

[57] ABSTRACT

A process for the preparation of p-hydroxybenzoic acid from p-methoxytoluene wherein said p-methoxytoluene is oxidized to p-anisic acid and said p-anisic acid is cleaved to p-hydroxybenzoic acid.

10 Claims, No Drawings

PROCESS FOR PREPARATION OF P-HYDROXYBENZOIC ACID FROM P-METHOXYTOLUENE

BACKGROUND OF THE INVENTION

The present invention relates to an improved process for the preparation of p-hydroxybenzoic acid. More particularly, the invention relates to an improved process for the preparation of p-hydroxybenzoic acid from p-methoxytoluene in high yield by oxidizing p-methoxytoluene to p-anisic acid and cleaving the methyl ether to form p-hydroxybenzoic acid.

p-Hydroxybenzoic acid is an important precursor for the preparation of p-acetoxybenzoic acid. p-Acetoxybenzoic acid is prepared from p-hydroxybenzoic acid by esterification of the hydroxy group with acetic acid or acetic anhydride. The acetylation step is normally quantitative, after the p-hydroxybenzoic acid has been purified, usually by crystallization. The purified p-acetoxybenzoic acid is an important monomer for production of liquid catalyst copolymers.

DESCRIPTION OF THE PRIOR ART

The oxidation of alkylaromatic compounds into oxygenated compounds in the liquid phase with molecular oxygen in the presence of a heavy metal catalyst has been disclosed. For example, U.S. Pat. No. 3,665,030 teaches that employing an oxidizing system comprising the higher valence cobalt(III) or higher valence manganese(III) salt of a carboxylic acid and a relatively strong acid provides a process for oxidation of alkylaromatic compounds in the liquid phase at temperatures within the range of $-30°$ to $+100°$ C. U.S. Pat. No. 3,665,030, in Example 24, discloses the oxidation of p-methoxytoluene by means of a catalytic system consisting of cobaltic acetate and trichloroacetic acid. Analysis of the ether extract indicated 56% of the p-methoxytoluene had been converted to yield, in mole percentages, p-methoxybenzyl alcohol (mainly in the form of acetate ester) 82%, and p-methoxybenzaldehyde, 18%. In another procedure, U.S. Pat. No. 4,297,520 discloses the oxidation of p-methoxytoluene with a dichromate ion forming substance and sulfuric acid to give anisaldehyde in good yields. The oxidation is reported to proceed with improved efficiency in the presence of a manganese compound. In an earlier disclosure, U.S. Pat. No. 3,985,809 taught the preparation of aromatic aldehydes and acids utilizing a manganese(III) salt to oxidize methoxytoluene to anisaldehyde, or, further, to the benzoic acid. The yield of anisaldehyde is taught as dependent upon maintaining a ratio of at least 2 to 1 methoxytoluene to anisaldehyde and controlling the temperature at the beginning of the oxidation at somewhat less than 20° C. and at no time allowing the temperature to rise above about 350° C. G.B. patent No. 798,619 discloses the oxidation of aralkyl compounds to aromatic carboxylic acids by passing oxygen or an oxygen-containing gas into a solution of an aralkyl compound in acetic acid in the presence of a cobaltous(II) catalyst at a temperature from about room temperature to 130° C, after initiating the reaction with ozone. The reaction is carried out preferably under as nearly anhydrous conditions as possible with an absolute maximum of about 0.1 part water per part acetic acid, since the presence of a large amount of water has an adverse effect upon the rate or reaction. When an amount of water in excess of about 0.1 part by weight per part of acetic acid is present, the reaction is essentially stopped. G.B. patent No. 842,998 discloses the oxidation of organic compounds for manufacture of aromatic carboxylic acids in liquid phase in the presence of a catalyst comprising manganese bromide and/or cobalt bromide. Preferably, the catalyst comprises mixed bromides of manganese and cobalt wherein the ratio of manganese to cobalt is about 2:1 although up to 9:1 gives good results. Suitable solvents which are taught comprise aliphatic carboxylic acids of 2 to 4 carbon atoms. Preferably the metal bromides are introduced into the reaction as such, although, if desired, the catalyst may be produced in situ by using salts of the metals which are soluble in the reaction mixture and introducing bromide or hydrobromic acid or an alkali metal bromide such as sodium. Temperatures of from ambient up to 300° C. can be used as well as the use of pressures up to 200 atmospheres gauge. Run times of 20 hours are taught in Examples 1 and 2 wherein the oxidation reaction temperature was at the boiling point of the mixture.

G.B. patent No. 842,998, in Example 4, teaches the oxidation of p-cresyl methylether (p-methoxytoluene) to p-anisic acid in a solvent of propionic acid, in the presence of a catalyst comprising 0.195 grams of $CoBr_2.6H_2O$ and 0.38 grams of $MnBr_2.4H_2O$. Molar conversion was 64.3%. The oxidation was conducted as described in Example 2 wherein run time was 20 hours. Mole ratio of cobalt:manganese was approximately 2:1. G.B. patent failed to recognize that a ratio of 1:1, cobalt to manganese, preferably a ratio of 1:>1 of cobalt to manganese, wherein the reaction was run at pressures of from 10 to 20 atmospheres and a temperature within the range of from about 200° F.–325° F., reduced run time from approximately 20 hours to approximately 30 to 45 minutes with yields of p-anisic acid of from about 79 to 85 mole %.

Cleavage of p-anisic acid in the presence of hydrogen bromide and acetic acid in a cleavage reaction produces p-hydroxymethylbenzoic acid in good yield.

SUMMARY OF THE INVENTION

A novel process is disclosed for preparation of p-hydroxybenzoic acid by oxidizing p-methoxytoluene to p-anisic acid and cleaving the acid to p-hydroxybenzoic acid. The improved yields and substantially decreased reaction time in preparing p-anisic acid are obtained by use of a catalyst comprising cobalt:manganese in a mole ratio of 1:1 or 1:>1, and bromine in a total weight ratio to p-methoxytoluene of about 0.10 to about 0.30 weight percent and total weight ratio of bromine ions to total metal ions is from about 0.7 to about 2.0, a pressure within the range of from atmospheric to about 30 atmospheres and a temperature within the range of from about 210° F. to 350° F., in the presence of a lower aliphatic carboxylic acid wherein weight ratio of said lower carboxylic acid to p-methoxytoluene is in the range of at least 1.8:1 to 2.0:1, and final weight ratio is from about 1.0–2.5:1. p-Anisic acid is cleaved to p-hydroxybenzoic acid in the presence of hydrogen bromide and acetic acid.

DETAILS OF THE INVENTION

According to the present invention there is provided a process for the production of p-hydroxybenzoic acid from p-methoxytoluene in higher yield and reduced reaction time over previously disclosed processes.

Under the conditions of the process, a reaction medium comprising an aliphatic saturated carboxylic acid of from 2 to 4 carbon atoms is essential, preferably acetic acid or propionic acid, more preferably acetic acid. It is further essential that the carboxylic acid be present in an initial ratio of at least 1.8:1 to 20:1, upon a weight basis, of the starting weight of p-methoxytoluene and that the final weight ratio of acid to p-methoxytoluene be from 1.0 to 2.5:1.

A process for oxidizing p-methoxytoluene to p-anisic acid is disclosed which comprises catalytic oxidation of p-methoxytoluene with oxygen or an oxygen-containing gas in the presence of acetic acid in an oxidation zone wherein liquid-phase conditions are maintained and wherein the final weight ratio of acetic acid to p-methoxytoluene is in the range of about 1.0–2.5:1.0 and the catalyst comprises one or more heavy metal oxidation catalysts comprising zirconium, cobalt and manganese to provide a concentration of about 0.2 to about 0.4 weight percent total metals based on p-methoxytoluene and a source of bromine, to provide a total of about 0.10 to about 0.30 weight percent total bromine based on p-methoxytoluene. Below a concentration of about 0.2 to about 0.4 weight percent total metals based on p-methoxytoluene, yield of product is reduced significantly although product can be prepared. Above a concentration of 0.4 weight percent, the amount is uneconomic and wastes catalyst. The total weight ratio of bromine ions to total catalyst metals ions is about 0.7 to about 2.0. The zirconium content is about 1% to about 5% and the manganese content is about 30% to about 49.5%, each metal by weight of the total metals and wherein the cobalt content is about 49.5 to about 69 weight percent. Temperature is in the range of from about 210° F. to about 350° F. Pressure is in the range of from atmospheric to about 30 atmospheres.

A process for the oxidation of p-methoxytoluene with molecular oxygen to p-anisic acid under liquid-phase conditions with oxygen or an oxygen-containing gas in the presence of a cobalt-manganese-bromine catalyst at a temperature in the range of from about 210° F. to about 350° F. is disclosed, wherein total metals, cobalt and manganese, are present in a ratio of from about 0.2 to about 0.4 weight percent, based on p-methoxytoluene, wherein total weight ratio of bromine to total metal ions is about 0.7 to about 2.0, cobalt content is from about 40 to 60 weight percent of total metals and manganese content is from about 40 to 60 weight percent of total metals. Pressure is in the range of from atmospheric to 30 atmospheres. Initial weight ratio of acetic acid to p-methoxytoluene is in the range of about 1.0–2.0:1.0 to 20:1 and final weight ratio of acetic acid to p-methoxytoluene is in the range of about 1.0–2.5:1.0. Although p-methoxytoluene can be oxidized with the instant catalyst system wherein acetic acid is present in a ratio of 1.0:3.3 at 100° C., the oxidation is impractical since the product is a difficult-to-handle solid. The process comprises conducting a continuous, semicontinuous or batch oxidation of the p-methoxytoluene.

The disadvantages of long reaction time, and consequent economic penalty, have been overcome by an improved mode of operation comprising a catalyst combination wherein the mole ratio of metal components, cobalt to manganese, is 1:1, a bromine to p-methoxytoluene weight ratio of 0.10 to about 0.30, and a pressure of from 10 to 20 atmospheres and a temperature of from 250° F. to 325° F., wherein an excess of acetic acid to p-methoxytoluene is present upon a weight basis of up to 20:1.

The process can be conducted batchwise as follows: the starting compound, the acetic acid solvent, and the catalyst components are introduced into a stirred titanium-clad autoclave. Oxygen or air is fed continuously through an air inlet.

In a continuous process, the reaction is conducted in a reactor provided with a column for refluxing into which the starting material, acetic acid, catalyst and oxygen, or air, are introduced continuously, and from which a portion of the reaction mixture is continuously withdrawn and passed to a filter centrifuge for recovery. The mother liquor is continuously recycled to the reactor.

In a specific embodiment, all components are charged to the reactor at or near oxidation initiation temperature, preferably at about 250° F. to about 325° F. and at a pressure to maintain liquid-phase conditions. Then pressurized air is injected into the reaction mixture and the reaction temperature is permitted to increase by heat evolved by the oxidation reaction to about 325° F. but not to exceed 400° F.

The total bromine can be from a single source of bromine, for example, ionic bromine sources (HBr, NaBr, NH$_4$Br, and the like) or from a combined form of bromine, for example, organic bromides such as benzylbromide, tetrabromoethane and others. An ionic form of bromine is preferred.

Accordingly, the novel process for production of p-hydroxybenzoic acid from p-methoxytoluene comprises: (a) liquid-phase oxidation of p-methoxytoluene to p-anisic acid with a source of molecular oxygen in the presence of a catalyst, in a solvent comprising a lower aliphatic saturated carboxylic acid, at a temperature within the range of from about 200° F. to about 350° F. and a pressure of from about atmospheric to about 30 atmospheres, wherein the said lower aliphatic saturated carboxylic acid is present in an initial amount of at least 1.0:3.3 to 20:1 weight ratio to said p-methoxytoluene and said lower aliphatic saturated carboxylic acid is present in a final amount of about 1.0:3.3 to 2.5:1.0 weight ratio to said p-methoxytoluene; (b) purification of the resulting p-anisic acid; and (c) cleavage of said p-anisic acid to form p-hydroxybenzoic acid. The catalyst comprises a cobalt(II) compound, a manganese(II) compound, a bromine compound, and, alternatively, a zirconium compound. If the catalyst contains a zirconium compound, zirconium is present in an amount of from about 1 to 5 weight percent, cobalt from about 49.5 to about 69 weight percent, manganese from about 49.5 to about 30 weight percent, and bromine is present in a weight ratio to p-methoxytoluene of about 0.10 to about 0.30 weight percent and total weight ratio of bromine ions to total metal ions of cobalt and manganese is from about 0.7 to about 2.0. If zirconium is not present in the catalyst, cobalt is present in an amount of from about 50 to 70 weight percent, manganese is present in an amount of from about 30 to 50 weight percent, and bromine is present in a weight ratio to p-methoxytoluene of about 0.10 to about 0.30 weight percent and total weight ratio of bromine ions to total metal ions of cobalt and manganese is from about 0.7 to about 2.0. The carboxylic acid can be selected from acetic acid and propionic acid. Acetic acid is preferred. The source of molecular oxygen preferably is air. In a specific application the molecular oxygen comprises air, the solvent comprises acetic acid, the said catalyst comprises cobalt and manganese in a mole ratio of 1:1, bromine is present in a weight ratio to p-methoxytoluene of 0.10 to 0.30; process temperature is in the range of from about 200° F. to about 350° F. and pressure is in the range of from about 10 to 20 atmospheres.

The novel process is exemplified by the following examples. These examples are exemplary only and are not meant to be construed as limiting.

EXAMPLE I

Two hundred and thirty (230) g. (1.89 moles) p-methylanisole, 399 g. (6.65 moles) acetic acid, 21 g. (1.17 moles) water, 1.73 g. (0.007 moles) Co(OAc)$_2$0, 1.7 g. (0.007 moles) Mn(OAc)$_2$.4H$_2$0 and 1.4 g. (0.014 moles) NaBr were combined in a two-liter titanium-clad autoclave. The reactor was heated to 250° F. and pressurized to 150 psi. The air rate was ramped up to reach a value of 0.78 scf/min after 15 minutes. During the oxidation the temperature and pressure were gradually increased to reach final values of 324° F. and 250 psi. The oxidation was complete after 30 minutes. Analysis of the reaction mixture showed p-anisic acid, 85 mole % yield, and p-anisaldehyde, 1.2 mole % yield.

EXAMPLE II

The oxidation of p-methylanisole was run as in Example I except that 2.29 g (0.014 moles) of 48% HBr were used in place of the NaBr, the air rate was adjusted in order to keep the vent oxygen concentration between 3 and 5 volume %, the final reaction temperature and pressure were 322° F. and 271 psi, and the run time was 36 minutes. The yield of p-anisic acid was 79 mole %, p-anisaldehyde, 1.6 mole % and p-methoxybenzylalcohol, 1.1 mole %. A 20 g sample of the reaction slurry which contained 33.4 wt % p-anisic acid (6.7 g.) was combined with 120 g. propionic acid and 10.2 g 48% HBr. The solution was refluxed at 114° C. for 120 hours and then cooled. The yield of p-hydroxybenzoic acid from the hydrolysis step was 96.5 mole %, with 3.5% p-anisic acid unreacted.

EXAMPLES III-VI

In the procedure of Example I, four oxidations were made with different sources of bromine. All other reaction conditions were virtually the same. Reaction conditions are in Table I, and results in Table II.

TABLE I

| Reaction Conditions for p-Methylanisole Oxidations | | | | |
|---|---|---|---|---|
| Example, No. | III | IV | V | VI |
| Run Number | 8500-132 | 8500-134 | 8500-142 | 8500-185 |
| p-Methylanisole, g | 230 | 230 | 230 | 230[a] |
| Acetic Acid, g | 399 | 399 | 399 | 399 |
| Water, g | 21 | 21 | 21 | 21 |
| Co(OAc)$_2$.4H$_2$O, g | 1.73 | 1.73 | 1.73 | 1.73 |
| Mn(OAc)$_2$.4H$_2$O, g | 1.70 | 1.70 | 1.70 | 1.70 |
| 48% HBr, g | — | — | 2.29 | — |
| Temperature, °F.[b] (Initial-Final) | 250-324 | 250-320 | 250-322 | 250-325 |
| Pressure, psi[c] (Initial-Final) | 150-250 | 150-300 | 150-275 | 150-300 |
| Air Rate, SCFM | 78[d] | CAD[e] | CAD | CAD |
| Run Time, minutes | 30 | 41 | 36 | 40 |

Notes:
[a] Fifteen grams p-methoxytoluene were charged into the reactor with the solvent and catalyst. The remaining 215 g were added during the first 27 minutes of reaction at a rate of 7.96 ml/minute.
[b] The same temperature profile was used in all of the reactions. The differences in final temperature are caused by the the different run times.
[c] The same pressure profile was used in each reaction. The differences in final pressure are caused by the different run times.
[d] A 15 minute air ramp was used up to the rate of 78 SCFM.
[e] Constant Air Demand. The air rate was adjusted to keep the vent oxygen level between 3% and 5%.

TABLE II

| Analyses of p-Methoxytoluene Oxidations | | | | |
|---|---|---|---|---|
| Example, No. | III | IV | V | VI |
| Run Number | 8500-132 | 8500-134 | 8500-142 | 8500-185 |
| p-Anisic Acid[a] | 85 | 84 | 79 | 82 |
| p-Anisaldehyde[a] | 1.2 | 1.4 | 1.6 | 1.5 |
| p-Methoxybenzyl alcohol[a] | <2.5 | 1.3 | 1.1 | 2.5 |
| p-Methoxytoluene[a] | <3.4 | <0.4 | <0.4 | 2.2 |
| Hydrocarbon Accountability (%)[b] | 86 | 87 | 82 | 88 |
| Mass Accountability (%)[c] | 89 | 93 | 94 | 95 |
| Purity of Dried Cake (%) | — | — | 89 | 96 |
| Purity of Recrystallized Product (%) | — | — | 95 | 98 |

Note:
[a] Reported as mole percent yield of p-methoxytoluene fed. The yields were determined by liquid chromatographic analysis of the TRE slurry.
[b] Not including burning losses.
[c] Assuming a 50:50 burning split between acetic acid and p-methoxytoluene, with one mole of the aromatic hydrocarbon being burned to 8 moles CO$_x$.

EXAMPLE VII p-Anisic acid was cleaved to p-hydroxybenzoic acid in the presence of hydrogen bromide and acetic acid. Details are in Table III. Other well-known methods of cleavage of methyl ethers can be used. Use of higher temperatures and increased pressure can increase the reaction rate. The following example wherein reaction time is 96 hours illustrates reaction time required for cleavage of p-anisic acid at comparatively low temperature and 1 atmosphere pressure.

TABLE III

| Conversion of p-Anisic Acid to p-Hydroxybenzoic Acid | |
|---|---|
| Run Number | 8500-191 |
| Reactants | 10 g dried total reactor effluent |
| | 11 g 48% HBr |
| | 150 ml acetic acid |
| Temperature, °C. | 105 |
| Time, hours | 96 |
| % Conversion to p-Hydroxybenzoic Acid | 82 |

EXAMPLE VIII

In the procedure of Example I, p-methoxytoluene was oxidized at a temperature within the range of from 400° F. to 410° F. Reaction pressure was 400 psi. The yield dropped, because of the higher temperature, to 20 mole % of p-anisic acid and 1.5 mole % of the aldehyde. Unreacted p-methoxytoluene was 4.5 mole %. A substantial amount of high molecular weight by-products such as methyl dimethoxydiphenyl methane and its oxidation products were produced. Reactor conditions and process results are in Table IV.

TABLE IV

| Oxidation of p-Methyoxytoluene at 400F.°–410° F. | |
|---|---|
| Reactor charge, g | |
| p-Methoxytoluene | 230 |
| Acetic acid | 399 |
| Water | 21 |
| Co(OAc)$_2$.4H$_2$O | 1.73 |
| Mn(OAc)$_2$.4H$_2$O | 1.70 |
| 48% HBr | 2.29 |
| Process Conditions | |
| Temp °F. | 400–410 |
| Pressure, psi | 400 |
| Run time, min. | 34 |
| Product Yields, Mole % | |
| p-Anisic acid | 20 |
| p-Anisaldehyde | 1.5 |
| p-Methoxybenzyl Alcohol | NA |
| p-Methoxytoluene | 4.5 |
| Hydrocarbon by-products | 40 |

The above results indicate that product yields decrease significantly with an increase in temperature to about 400° F.

What is claimed is:

1. A process for production of p-hydroxybenzoic acid from p-methoxytoluene in high yield, which process comprises:
    (a) liquid-phase oxidation of p-methoxytoluene to p-anisic acid with a source of molecular oxygen in the presence of a catalyst wherein said catalyst comprises a cobalt(II) compound, a manganese(II) compound and a bromine compound, in a solvent comprising a lower aliphatic saturated carboxylic acid, at a temperature within the range of from about 200° F. to about 350° F. and a pressure from about atmospheric to about 30 atmospheres,
    (b) purification of said p-anisic acid; and
    (c) cleavage of said p-anisic acid to p-hydroxybenzoic acid, the improvement in combination therewith comprising said catalyst comprising cobalt:manganese in a mole ratio of 1:1 or 1:>1, said bromine in a total weight ratio to said p-methoxytoluene of about 0.10 to about 0.30 weight percent and total weight ratio of bromine ions to total metal ions is from about 0.7 to about 2.0, said lower aliphatic carboxylic acid is present in an initial amount of at least 1.0:3.3 to 20:1 weight ratio to said p-methoxytoluene, and said lower aliphatic carboxylic acid is present in a final amount of about 1.0:3.3 to 2.5:1.0 weight ratio to said p-methoxytoluene.

2. The process of claim 1 wherein said catalyst comprises a cobalt(II) compound, a manganese(II) compound, a zirconium compound, and a bromine compound.

3. The process of claim 2 wherein cobalt content of said catalyst is from about 49.5 to about 69 weight percent, manganese content is from about 49.5 to about 30 weight percent, zirconium content is from about 1 to 5 weight percent, and bromine is present in a weight ratio to p-methoxytoluene of about 0.10 to about 0.30 weight percent and total weight ratio of bromine ions to total metal ions of cobalt and manganese is from about 0.7 to about 2.0.

4. The process of claim 1 wherein cobalt content of said catalyst is from about 50 to about 70 weight percent, manganese content is from about 50 to about 30 weight percent and bromine is present in a weight ratio to p-methoxytoluene of about 0.10 to about 0.30 weight percent and total weight ratio of bromine ions to total metal ions of cobalt and manganese is from about 0.7 to about 2.0.

5. The process of claim 1 wherein said lower aliphatic carboxylic acid is selected from the group consisting of acetic acid and propionic acid.

6. The process of claim 1 wherein said source of molecular oxygen comprises air.

7. The process of claim 1 wherein said process is a batch process.

8. The process of claim 1 wherein said process is a semicontinuous process.

9. The process of claim 1 wherein said process is a continuous process.

10. The process of claim 1 wherein said source of molecular oxygen comprises air, said solvent comprises acetic acid, said catalyst comprises cobalt, manganese and bromine, said cobalt and manganese is in a mole ratio of 1:1, said bromine is in a weight ratio to p-methoxytoluene of 0.10 to 0.30, said process temperature is in the range of from about 200° F. to 350° F. and said pressure is in the range of from about 10 to 20 atmospheres.

* * * * *

UNITED STATES PATENT OFFICE
CERTIFICATE OF CORRECTION

Patent No. 4,740,614   Dated April 26, 1988

Inventor(s) Kristi A. Fjare

It is certified that error appears in the above-identified patent and that said Letters Patent are hereby corrected as shown below:

| Patent Column | Line | |
|---|---|---|
| 1 | 67 | reads "or" and should read --of-- |
| 5 | 15 | reads "$Co(OAc)_2O$," and should read --$Co(OAc)_2 \cdot 4H_2O$-- |
| 5 | 63 | NaBr, g line left out of Table I under "Example, No." |

Signed and Sealed this

Thirteenth Day of December, 1988

Attest:

DONALD J. QUIGG

Attesting Officer  Commissioner of Patents and Trademarks